(12) United States Patent
Koivusalmi et al.

(10) Patent No.: US 7,459,597 B2
(45) Date of Patent: Dec. 2, 2008

(54) PROCESS FOR THE MANUFACTURE OF HYDROCARBONS

(75) Inventors: Eija Koivusalmi, Kulloonkylä (FI); Juha Jakkula, Kerava (FI)

(73) Assignee: Neste Oil Oyj, Espoo (FI)

( * ) Notice: Subject to any disclaimer, the term of this patent is extended or adjusted under 35 U.S.C. 154(b) by 0 days.

(21) Appl. No.: 11/637,176

(22) Filed: Dec. 12, 2006

(65) Prior Publication Data

US 2007/0135669 A1 Jun. 14, 2007

Related U.S. Application Data

(60) Provisional application No. 60/749,581, filed on Dec. 13, 2005.

(51) Int. Cl.
*C07C 1/207* (2006.01)
*C07C 1/213* (2006.01)

(52) U.S. Cl. .................. 585/733; 585/930; 585/932

(58) Field of Classification Search .................. 585/733, 585/930, 932
See application file for complete search history.

(56) References Cited

U.S. PATENT DOCUMENTS

| | | | |
|---|---|---|---|
| 4,554,397 A | 11/1985 | Stern et al. | |
| 5,856,539 A | 1/1999 | Hodgson et al. | |

FOREIGN PATENT DOCUMENTS

| | | |
|---|---|---|
| EP | 1396531 A2 | 3/2004 |
| EP | 1396531 A3 | 3/2004 |
| EP | 1398364 A1 | 3/2004 |
| FI | 100248 B | 10/1997 |

OTHER PUBLICATIONS

Laurent et al. "Study of the hydrodeoxygenation of carbonyl, carboxylic and guaiacyl groups over sulfided CoMo/γ-$Al_2O_3$ and NiMo/γ-$Al_2O_3$ catalysts. I. Catalytic reaction schemes," Applied Catalysis, A: General 1994, 109(1), pp. 77-96.
Laurent et al. "Study of the hydrodeoxygenation of carbonyl, carboxylic and guaiacyl groups over sulfided CoMo/γ-$Al_2O_3$ and NiMo/γ-$Al_2O_3$ catalysts. II. Influenece of water, ammonia and hydrogen sulfide," Applied Catalysis, A: General 1994, 109(1), pp. 97-115.
Maier et al., "Gas phase decarboxylation of carboxylic acids," Chem. Ber., (1982), 115(2), pp. 808-812.
English translation of FI-100248-B, published on Oct. 31, 1997.

*Primary Examiner*—Thuan Dinh Dang
(74) *Attorney, Agent, or Firm*—Birch, Stewart, Kolasch & Birch, LLP

(57) ABSTRACT

A feedstock originating from renewable sources is converted to branched and saturated hydrocarbons without heteroatoms in the diesel fuel distillation range by skeletal isomerisation and deoxygenation carried out by hydrodeoxygenation or alternatively by combined decarboxylation and decarbonylation reactions, whereby the consumption of hydrogen is decreased.

31 Claims, No Drawings

PROCESS FOR THE MANUFACTURE OF HYDROCARBONS

This Non-provisional application claims priority under 35 U.S.C. § 119(a) on Patent Application No. 60/749,581 filed in United States of America on Dec. 13, 2005, the entire contents of which are hereby incorporated by reference.

FIELD OF THE INVENTION

The present invention relates to a process for the manufacture of hydrocarbons, particularly branched hydrocarbons from renewable sources and to a process for the manufacture of hydrocarbons, suitable for diesel fuel pool. The process comprises a skeletal isomerisation step and a deoxygenation step carried out by decarboxylation/decarbonylation or hydrodeoxygenation.

BACKGROUND OF THE INVENTION

Fatty acids have been used as raw materials in various applications in the chemical industry, typically in the manufacture of products ranging from lubricants, polymers, fuels and solvents to cosmetics. Fatty acids are generally obtained from wood pulping processes or by hydrolysis of triglycerides of vegetable or animal origin. Naturally occurring triglycerides are usually esters of glycerol and straight chain, even numbered carboxylic acids having 10-26 carbon atoms. Most common fatty acids contain 16, 18, 20 or 22 carbon atoms. Fatty acids may either be saturated or they may contain one or more unsaturated bonds. Unsaturated fatty acids are often olefinic having carbon-carbon double bonds with cis configuration. The unsaturated centres appear in preferred positions in the carbon chain. The most common position is ω9, like in oleic acic (C18:1) and erucic acid (C22:1). Poly-unsaturated acids generally have a methylene-interrupted arrangement of cis-olefinic double bonds.

Saturated long straight chain fatty acids (C10:0 and higher) are solid at room temperature, which makes their processing and use difficult in a number of applications. Unsaturated long chain fatty acids like e.g. oleic acid are easily processable liquids at room temperature, but they are unstable because of double bond(s).

Branched fatty acids mimic the properties of straight chain unsaturated fatty acids in many respects, but they are more stable. For example branched C18:0 fatty acid, known as isostearic acid, is liquid at room temperature, but it is not as unstable as C18:1 acid, since the unsaturated bonds are absent in branched C18:0. Therefore, branched fatty acids are more desirable for many applications than straight chain fatty acids.

Diesel fuels based on biological material are generally referred to as biodiesel. A definition for "biodiesel" is provided in Original Equipment Manufacturer (OEM) guidelines as follows: Biodiesel is mono-alkyl esters of long chain fatty acids derived from vegetable oils or animal fats, which conform to ASTM D6751 or EN 14214 specification for use in diesel engines as described in following Table 1. Biodiesel refers to pure fuel before blending with diesel fuel (B100).

TABLE 1

Specification for Biodiesel (B100, 100%)

| Property | ASTM D6751 | EN 14214 | Units |
|---|---|---|---|
| Density at 15° C. | | 860-900 | kg/m³ |
| Flash point (closed cup) | 130 | ≧120 | ° C. |
| Water and sediment | ≦0.050 | ≦0.050 | % |
| Kinematic viscosity 40° C. | 1.9-6.0 | 3.5-5.0 | mm²/s |
| Sulfated ash | ≦0.020 | ≦0.020 | % mass |
| Sulfur | ≦0.05 | ≦0.001 | % mass |
| Cetane number | ≧47 | ≧51 | |
| Carbon residue | ≦0.050 | | % mass |
| Carbon residue 10% dist bottom | | ≦0.3 | % mass |
| Acid number | ≦0.80 | ≦0.5 | mg KOH/g |
| Free glycerol | ≦0.020 | ≦0.02 | % mass |
| Total glycerol | ≦0.240 | ≦0.25 | % mass |
| Phosphorus content | ≦0.001 | ≦0.001 | % mass |

High cetane number, proper viscosity range and good low-temperature properties are required for a good diesel fuel. Cetane number (CN) has been established for describing the ignition quality of diesel fuel or its components. Branching and chain length influence CN, the CN decreasing with decreasing chain length and increasing branching. Hexadecane $C_{16}H_{34}$ has a CN of 100, and 2,2,4,4,6,8,8-heptamethylnonane $C_{16}H_{34}$ has a CN of 15. From structural features also double bonds decrease CN. Further, compounds with unsaturation can cause gumming in engines.

Besides CN, gross heat of combustion (HG) of a compound is essential in providing the suitability of the compound to be used as diesel fuel. For comparison the HGs of paraffinic and ester biodiesels are as follows: HG of hexadecane is 2559 kg cal/mol at 20° C. and of methyl palmitate (C16:0) 2550 kg cal/mol.

Cloud point presents the temperature where a petroleum product shows just a cloud or haze of wax crystals when it is cooled under standard test conditions, as described in standard ASTM D2500. Cloud point measures the ability of the fuel to be used in cold weather without plugging filters and supply lines.

Pour point is the lowest temperature at which a fuel will just flow when tested under the conditions described in standard ASTM D97. It is recommended by engine manufacturers that the cloud point should be below the temperature of use and not more than 6° C. above the pour point. Branching, saturation and chain length influence also cloud and pour points and they decrease with decreasing chain length, increasing unsaturation and increasing branching.

The viscosity of vegetable oils is approximately one order of magnitude greater than that of conventional diesel fuels. High viscosity results in poor atomization in combustion chamber, thus causing coking of nozzles and deposits.

Biodiesel is an alternative fuel, produced from renewable sources and it contains no petroleum. It can be blended in minor amounts with petroleum diesel to create a biodiesel blend, further it is non-toxic and essentially free of sulfur and aromatics. It can be used in compression-ignition (diesel) engines with little or no modifications. Diesel fuels based on biological material have been demonstrated to have significant environmental benefits in terms of decreased global warming impacts, reduced emissions, greater energy independence and a positive impact on agriculture.

It has been demonstrated that the use of diesel fuels based on biological material will result in a significant reduction in carbon dioxide emissions. A biodiesel lifecycle study of 1998, jointly sponsored by the US Department of Energy and the US Department of Agriculture, concluded that biodiesel reduces net $CO_2$ emissions by 78 percent compared to petroleum diesel. This is due to biodiesel's closed carbon cycle. $CO_2$, released into the atmosphere when burning biodiesel, is recycled by growing plants, which are later processed into fuel. As such, the increased use of diesel fuels based on biological material represents an important step to meet the emission reduction target as agreed under the Kyoto agreement. It is also believed that particulate emissions and other harmful emissions, such as nitrogen oxides, alleviating human health problems, are reduced.

Methyl esters of long-chain acids have higher cloud and pour points than the corresponding triglycerides and conventional diesel fuels. Cloud and pour points are important features when operating engines in cooler environment.

Several approaches, as such transesterification, dilution, micro-emulsification and co-solvent blending, as well as pyrolysis have been suggested for obtaining diesel fuel from vegetable oils and other triacylglycerol based feedstocks. The object of said approaches is to reduce the high kinematic viscosity of neat vegetable oils, which can cause severe operational problems and improper atomization of the fuel.

In transesterification, triglycerides forming the main component in vegetable oils are converted into the corresponding esters with an alcohol in the presence of catalysts. Methanol is the most commonly used alcohol due to its low cost and easy separation from the resulting methyl ester and glycerol phases.

Diluting 0-34% of vegetable oils with conventional diesel fuel leads to proper atomization but causes engine problems similar to those with neat vegetable oils.

Micro-emulsion fuels are composed of conventional diesel fuel and/or vegetable oil, a simple alcohol, an amphiphilic compound such as a surfactant and a cetane improver. Trace quantities of water are usually required for formation of the microemulsion.

Pyrolytic methods, Kolbe electrolysis and thermal and catalytic cracking of bio-materials like vegetable oils, their methyl esters and animal fats result in a wide spectrum of products, such as alkanes, alkenes, aromatics and carboxylic acids. The reactions are generally unselective and less valuable by-products are formed too.

Unsaturated and aromatic hydrocarbons present in the liquid fraction make the products obtained by the above methods unattractive for the diesel pool. Poor low-temperature properties of the products limit their wider use as biodiesel in regions with colder climatic conditions. In addition, the presence of oxygen in esters results in undesirable higher nitrogen oxide ($NO_x$) emissions compared to conventional diesel fuels.

Sulphur free fuels are required in order to gain the full effect of new and efficient anti-pollution technologies in modern vehicles and to cut emissions of nitrogen oxides, volatile hydrocarbons and particles, as well as to achieve direct reduction of sulphur dioxide in exhaust gases. The European Union has decreed that these products must be available to the market from 2005 and must be the only form on sale from 2009. This new requirement will reduce annual sulphur emissions from automotive fuels.

Branched fatty acids and fatty acid esters, mainly methyl and ethyl esters, are obtained by isomerisation of straight chain, unsaturated fatty acids and fatty acid esters having a corresponding chain length, as described in U.S. Pat. No. 5,856,539. For example, branched C18:0 acids are prepared from straight chain C18:1 acids or also C18:2 acids.

Decarboxylation of carboxylic acids to hydrocarbons by contacting carboxylic acids with heterogeneous catalysts was suggested by Maier, W. F. et al: *Chemische Berichte* (1982), 115(2), 808-12. $Ni/Al_2O_3$ and $Pd/SiO_2$ catalysts were tested for decarboxylation of several carboxylic acids. During the reaction the vapours of the reactant passed through a catalytic bed together with hydrogen at 180° C. and 0.1 MPa. Hexane represented the main product of the decarboxylation of heptanoic acid. When nitrogen was used instead of hydrogen no decarboxylation was observed.

U.S. Pat. No. 4,554,397 discloses a process for the manufacture of linear olefins from saturated fatty acids or esters by decarboxylation using a catalytic system, which consists of nickel and at least one metal selected from the group consisting of lead, tin and germanium. Additives may be included in the above-mentioned catalysts and for example sulphur derivatives may be added to decrease the hydrogenating power of nickel and make the reaction more selective for olefin formation reaction. The presence of hydrogen was necessary to maintain the activity of the catalyst. The reaction was carried out at a temperature of 300-380° C. and the pressure was atmospheric pressure or higher.

Decarboxylation accompanied with hydrogenation of oxo-compound is described in Laurent, E., Delmon, B.: *Applied Catalysis*, A: General (1994), 109(1), 77-96 and 97-115, wherein hydrodeoxygenation of biomass derived pyrolysis oils over sulphided $CoMo/Al_2O_3$ and $NiMo/Al_2O_3$ catalysts was studied. Hydrotreating conditions were 260-300° C. and 7 MPa in hydrogen. The presence of hydrogen sulphide promoted the decarboxylation, particularly when a NiMo catalyst was used.

Unsaturated and aromatic hydrocarbons produced in the side reactions in the above-mentioned processes make the obtained products unattractive for the diesel pool. In addition, the unbranched and highly saturated structures cause poor low-temperature properties.

FI 100248 describes a two-step process for producing middle distillate from vegetable oil by hydrogenating fatty acids or triglycerides of vegetable oil using commercial sulphur removal catalysts (NiMo and CoMo) to give n-paraffins and then by isomerising said n-paraffins using metal containing molecule sieves or zeolites to obtain branched-chain paraffins. The hydrotreating was carried out at reaction temperatures of 330-450° C.

Based on the above it can be seen that here is a need for a new alternative process for the preparation of saturated and branched hydrocarbons from renewable sources, suitable as biodiesel of high quality.

OBJECT OF THE INVENTION

An object of the invention is a process for the manufacture of branched saturated hydrocarbons from renewable sources.

A further object of the invention is a process for the manufacture of branched saturated hydrocarbons suitable for the diesel fuel pool.

Characteristic features of the process according to the invention are provided in the claims.

DEFINITIONS

Skeletal isomerisation is understood to mean formation of branches in the main carbon chain while the carbon number of the compound is not altered.

Deoxygenation is understood to mean removal of carboxyl oxygen, such as fatty acid or fatty acid ester oxygen. Deoxygenation may be carried out by hydrodeoxygenation (HDO) or decarboxylation/decarbonylation.

Decarboxylation/decarbonylation is understood to mean removal of carboxyl oxygen through $CO_2$ (decarboxylation) and/or through CO (decarbonylation).

Hydrodeoxygenation (HDO) means removal of oxygen as water using hydrogen.

The term "branched fatty acids" is herein to be understood to comprise fatty acids containing one or more alkyl side groups, which can be attached to the carbon chain at any position. Said alkyl groups are generally $C_1$-$C_4$ alkyl chains.

Pressures are here understood to mean overpressures above atmospheric pressure.

SUMMARY OF THE INVENTION

The present invention relates to a catalytic process for the manufacture of branched saturated hydrocarbons, which are suitable for diesel fuel pool, from renewable sources, such as plant, vegetable, animal and fish fats and oils and fatty acids. The invention concerns the transformation of a feedstock comprising fatty acids or fatty acid esters with lower alcohols into branched fatty acids or fatty acid esters with a acidic catalyst, followed by converting the obtained branched fatty acids or fatty acid esters into branched hydrocarbons either by contacting with a heterogeneous decarboxylation/decarbonylation catalyst or with a hydrodeoxygenation catalyst.

The branched hydrocarbon product formed via the decarboxylation/decarbonylation reaction has one carbon atom less than the original fatty acid, and the branched hydrocarbon product formed via the hydrodeoxygenation reaction has an equal number of carbon atoms compared to the original fatty acid.

A high quality hydrocarbon product with good low temperature properties and high cetane number is obtained, employing minimum amount of hydrogen in the process.

DETAILED DESCRIPTION OF THE INVENTION

It has now been surprisingly found that saturated and branched hydrocarbon, suitable for biodiesel fuel, can be obtained from oxygen containing feedstocks originating from renewable sources by skeletal isomerisation followed by removal of oxygen utilising deoxygenation carried out by decarboxylation/decarbonylation or hydrodeoxygenation.

In the first process step a feedstock comprising unsaturated fatty acids or fatty acid esters with lower alcohols, or mixtures thereof are subjected to skeletal isomerisation wherein they are isomerised to fatty acids or fatty acid alkyl esters containing short alkyl branches in their carbon chain. In the subsequent process step the branched products are deoxygenated. The deoxygenation is carried out by decarboxylation/decarbonylation wherein oxygen is removed in the form of CO and $CO_2$, or alternatively by hydrodeoxygenation wherein oxygen is removed in the form of $H_2O$ from the isomerised fatty acids or fatty acid alkyl esters. The process may also comprise an optional prehydrogenation step before the deoxygenation step to remove unsaturation after skeletal isomerisation and to liberate lower alcohol in hydrodeoxygenation.

The process according to the invention provides a convenient way for the manufacture of branched hydrocarbons from fatty acids or fatty acid esters with lower alcohols. The fatty acid and fatty acid esters originate from biological feedstock such as plant, vegetable, animal and fish oils and fats.

Feedstock

The feedstock comprises fatty acids or fatty acid esters with $C_1$-$C_5$, preferably $C_1$-$C_3$ alcohols, or mixtures thereof. The feedstock preferably originates from biological raw materials such as plant, vegetable, animal and fish oils and fats. Biological raw materials my be treated using any pretreatment or purification method known in the art to obtain the fatty acids or fatty acid esters useful as the feedstock, such as hydrolysis etc. The feedstock comprises at least 20% by weight, preferably at least 50% by weight and particularly preferably 80% by weight of unsaturated fatty acids or fatty acid esters. The feedstock may also comprise mixtures of fatty acids and fatty acid esters, but it is preferable to use either fatty acids or fatty acid esters.

The unsaturated fatty acid used as the feedstock is a fatty acid having unsaturated bonds and a total carbon number of 8 to 26, preferably 12 to 20 and particularly preferably 12 to 18. With respect to the degree of unsaturation, i.e., the number of unsaturated carbon-carbon bonds, any unsaturated fatty acids may be used as long as one or more unsaturated carbon-carbon are present in the molecule.

The feedstock may comprise $C_1$-$C_5$, preferably $C_1$-$C_3$ alkyl esters of unsaturated fatty acids having a total carbon number of 8-26, preferably 12-20 and particularly preferably 12-18, corresponding to the above-mentioned unsaturated fatty acids. Examples of suitable alkyl esters include methyl esters, ethyl esters and propyl esters of said unsaturated fatty acids, with preference given to methyl esters.

Typically, the number of unsaturated bonds in the feedstock is 1 to 3. Preferably the feedstock comprises at least 40% by weight of monounsaturated fatty acids or fatty acid esters, more preferably at least 70% by weight. The feedstock may also comprise polyunsaturated fatty acids or fatty acid esters. The presence of an unsaturated bond in the molecule causes the formation of a cation as an intermediate, thereby facilitating the skeletal isomerisation reaction.

Skeletal Isomerisation

In the first step of the process according to the present invention branched chain fatty acids or alkyl esters of fatty acids are prepared. The earlier described feedstock is subjected to a skeletal isomerisation step. The skeletal isomerisation is carried out at a temperature of 150-400° C., under the pressure of 0-5 MPa, preferably at 200-350° C. and 0.1-5 MPa and particularly preferably at 220-300° C. and 0.1-2 MPa using an acidic catalyst. Suitable acidic catalysts are silico alumino phosphates and zeolites, preferably faujasite, offeretite, montmorillonite and mordenite. Particularly preferably the catalyst is mordenite.

Water or a lower alcohol may be added to the feedstock to suppress acid anhydride formation due to dehydration or dealcoholation. It is preferable to add water when the feedstock comprises unsaturated fatty acids and alcohol when the feedstock comprises esters of unsaturated fatty acids. Typically the amount of added water or lower alcohol is 0-8%, and preferably 1-3% by weight based on the total reaction mixture. The lower alcohol is $C_1$-$C_5$ alcohol, and preferable alcohols are methanol, ethanol and propanol, with a greater preference given to those having the same alkyl group as that of the starting fatty acid ester to be isomerised. Excess water (more than 10%) should be avoided in order to prevent estolide formation. The skeletal isomerisation step may also be carried out in the absence of water or lower alcohol.

The skeletal isomerisation step may be carried out in a closed batch reactor under the reaction pressure. This is to prevent vaporization of water, alcohols and other low boiling substances in the system, including those substances contained in a catalyst. The reaction time is preferably less than 24 hours, more preferably less than 12 hours and most preferably less than 30 minutes.

In general, the amount of catalyst employed in the process is 0.01-30% by weight based on the total reaction mixture, preferably the amount of catalyst used is 1-10% by weight.

When a continuous flow reactor is used the space velocity WHSV is 0.1-100 l/h, more preferably 0.1-50 l/h and most preferably 1-10 l/h.

The product from the skeletal isomerisation step contains both saturated as well as unsaturated branched chain fatty acids or esters of fatty acids. Possible by-products are cyclic acids and polymeric fatty acids, such as dimer acids and polymeric fatty acid esters, when the feedstock comprises esters of unsaturated fatty acids. The obtained branched chain compounds normally have short alkyl side chains, the length being from 1 to 4 carbon atoms and they are obtained as mixtures of many isomers with different branching positions.

Preferably, the obtained branched chain fatty acids or fatty acid esters are separated from dimer acids for example by distillation, their unsaturated bonds are prehydrogenated and then separated from linear, saturated alkyl fatty acids or their esters by solvent fractionation. The order of distillation, prehydrogenation and fractionation may be changed. Distillation and solvent fractionation steps may also be at the end of the process after deoxygenation.

The skeletal isomerisation product may optionally be prehydrogenated in order to remove unsaturation, which may cause formation of coke on the catalyst surface in the subsequent catalytic steps. The prehydrogenation is carried out in the presence of a hydrogenation catalyst at a temperature 50-400° C. under a hydrogen pressure of 0.1-20 MPa, preferably at 150-250° C. and 1-10 MPa. The heterogeneous hydrogenation catalyst contains one or more Group VIII and/or VIA metals. Preferably the hydrogenation catalyst is Pd-, Pt-, Ni-, NiMo- or CoMo-catalyst on aluminum and/or silicon oxide support.

In the case where fatty acid esters are used as feedstock in the isomerisation step, the branched product from skeletal isomerisation may optionally be prehydrogenated before the final deoxygenation step to saturate the double bonds and to liberate the lower alcohol used in esterification. Fatty acid alkylesters are converted to fatty alcohols for hydrodeoxygenation. Liberated lower alcohol may be recycled after distillation. Fatty acid alkylesters are prehydrogenated with metal catalysts at 25-30 MPa hydrogen pressure and at temperature of 200-230° C. The metal catalyst is preferably copper-chromite catalyst or chrome, ferrous or rhodium activated nickel catalyst.

Deoxygenation

The branched product obtained from the skeletal isomerisation step is then subjected to deoxygenation carried out by decarboxylation/decarbonylation or hydrodeoxygenation.

In the first embodiment, the saturated and branched fatty acids or esters of fatty acids and optionally a solvent or a mixture of solvents are brought into contact with a heterogeneous decarboxylation/decarbonylation catalyst selected from supported catalysts containing one or more Group VIII and/or VIA metals of the Periodic System. Preferably, the decarboxylation/decarbonylation catalysts are supported Pd, Pt, Ni, NiMo or a CoMo catalysts, the support being alumina and/or silica and/or carbon. Particularly preferably Pd on carbon and sulphided NiMo on alumina are used. Hydrogen may optionally be used. The decarboxylation/decarbonylation reaction conditions may vary with the feedstock used. The reaction is carried out in liquid phase. The decarboxylation/decarbonylation reaction is carried out at a temperature of 100-400° C., preferably 250-350° C. The reaction may be conducted under atmospheric pressure. However, in order to maintain the reactants in the liquid phase it is preferable to use higher pressure than the saturation vapour pressure of the feedstock at a given reaction temperature and thus the reaction pressure ranges from atmospheric pressure to 20 MPa and preferably from 0.1 to 5 MPa of inert gas/hydrogen mixture. The product obtained from this embodiment is a mixture of hydrocarbons, preferably branched paraffins boiling in the range of 180-350° C., the diesel fuel range, and having one carbon atom less than the original fatty acid chain.

In the second embodiment, in the hydrodeoxygenation step the branched fatty acids or esters thereof obtained from the skeletal isomerisation step, or the fatty alcohols obtained by the optional prehydrogenation step, and optionally a solvent or a mixture of solvents are brought into contact with an optionally pre-treated heterogeneous hydrogenation catalysts containing metals from Group VIII and/ or VIA of the Periodic System, known in the art for hydrodeoxygenation. Preferably, the hydrodeoxygenation catalysts are supported Pd, Pt, Ni, NiMo or a CoMo catalysts, the support being alumina and/or silica. Particularly preferably NiMo/$Al_2O_3$ and CoMo/$Al_2O_3$ catalysts are used. In the hydrodeoxygenation step, the pressure range can be varied between 1 and 20 MPa, preferably 2-10 MPa, and the temperature 200-500° C., preferably 250-350° C.

The optional solvent in each deoxygenation embodiment can be selected from the group consisting of hydrocarbons, such as paraffins, isoparaffins, naphthenes and aromatic hydrocarbons in the boiling range of 150-350° C., and recycled process streams containing hydrocarbons, and mixtures thereof, preferably the recycled product streams obtained from the process according to the invention are used.

Product

The process according to the invention yields a branched and paraffinic hydrocarbon product suitable for diesel fuel pool. The product contains typically some short carbon-carbon side branches, resulting in an exceptionally low cloud point and cold filter plugging point but still a good cetane number compared to the products obtained by the known methods. In Table 2 properties of the product produced with the process according to the invention (1) are compared to those obtained by processes according to the state of the art (2-6). All products are 100% (B100) diesel components.

TABLE 2

| Property | | Product 1 | Product 2 | Product 3 | Product 4 | Product 5 | Product 6 |
|---|---|---|---|---|---|---|---|
| kV40 $mm^2$/s | | 2.4-4.4 | 2.9-3.5 | 4.5 | 3.2-4.5 | 2.0-4.5 | 1.2-4.0 |
| Cloud point ° C. | | −29--42 | −5--30 | −5 | 0--25 | | −10--34 |
| Flash point PMcc, ° C. | | 67-141 | 52-65 | | | ≧55 | |
| Cold filter plug point, ° C. | | −31--45 | −15--19 | | | ≦+5--20 | ≦−20--44 |
| IQT cetane number | | 60-93 | 84-99 | 51 | 73-81 | ≧51 | ≧51 |
| Sulfur ppm | | <10 | <10 | <10 | <10 | <10 | <10 |
| Density 15° C. kg/$m^3$ | | 799-811 | 775-785 | 885 | 770-785 | 820-845 | 800-840 |
| Dist. | 10% | 195-286 | 260-270 | 340 | 260 | | 180 |
| | 90% | 301-337 | 295-300 | 355 | 325-330 | | |
| | 95% | 312-443 | | | | 360 | 340 |

The products of Table 2 are prepared as follows:
(1) is prepared by the method according to the invention, by skeletal isomerisation and deoxygenation of fatty acids
(2) is prepared by hydrodeoxygenation and hydroisomerisation of triglycerides
(3) is fatty acid methyl ester prepared by transesterification of rape seed oil
(4) is natural gas based diesel fuel prepared by gas to liquid and hydroisomerisation processes
(5) and (6) are mineral oil based diesel fuels with different specifications for use in the arctic conditions The structure of the branched, saturated hydrocarbon product obtained using the process according to the invention is different from the one obtained for example when hydroisomerising C16-C22 normal paraffins. In the present case the branches are mainly in the middle of the long carbon chain, due to the common ω9 olefinic unsaturation positions responsible of branching. In the hydroisomerised isoparaffins, the branches are mainly near the end of the carbon main chain. The carbon number of the hydrocarbon product of the invention is C13-C22, typically C15-C18 and the carbon number in the product can be adjusted by changing the hydodeoxygenation and/or decarboxylation/decarbonylation reaction conditions.

The branched, saturated hydrocarbon product contains paraffins more than 80 vol-%, typically more than 99 vol-%.

The branched, saturated hydrocarbon product contains n-paraffins less than 30 wt-%, typically less than 15 wt-%.

The branched, saturated hydrocarbon product contains aromatics less than 20 vol-%, typically less than 10 vol-% according to method IP-391.

Biodiesel components also contain $^{14}C$-isotope, which can be used as an evidence of the bio origin of the fuel. The typical $^{14}C$ content of the branched, saturated hydrocarbon product is at least 100% based on radiocarbon content compared to radiocarbon content of air in the year 1950.

The process according to the invention has several advantages. With the process, a branched, saturated hydrocarbon product comprising branched chains and suitable for the diesel fuel pool is obtained from renewable sources. Due to the absence of unsaturation in the hydrocarbon product, the oxidation stability is good and the tendency for polymerisation low compared to the conventional fatty acid methyl ester based biodiesel compounds. Branching in the paraffinic carbon chain enhances low temperature properties, such as cloud point, pour point and cold-filter plugging point. The extremely good low temperature properties make it possible to use the branched, saturated hydrocarbon product as diesel fuel or diesel fuel component also in arctic fuels.

The branched, saturated hydrocarbon products manufactured according to the invention are designed for use in compression-ignition engines, where air is compressed until it is heated above the auto-ignition temperature of diesel fuel and then the fuel is injected as a high pressure spray, keeping the fuel-air mix within the flammable limits of diesel. Because there is no ignition source, the diesel fuel is required to have a high cetane number and a low auto-ignition temperature.

Due to saturation and long paraffinic chain length, the cetane number of the branched, saturated hydrocarbon product is high, thus making the product suitable as cetane number improver. The cetane number gauges the ease with which the diesel fuel will auto-ignite when compressed. Higher cetane numbers indicate easier self-ignition and better engine operation.

The high flash point of the branched, saturated hydrocarbon product is important primarily from a fuel-handling standpoint. In the ethanol/mineral oil diesel or ethanol/vegetable oil diesel micro-emulsions, the flash point is remarkably lower. A too low flash point will cause fuel to be a fire hazard, subject to flashing, and possible continued ignition and explosion. In addition, a low flash point may indicate contamination by more volatile and explosive fuels, such as gasoline.

Because of the natural fatty acid based raw materials, the branched, saturated hydrocarbon product contains no sulphur. Thus, in the pretreatment of exhaust gas the catalysts and particulate filters can easily be adjusted to the sulphur-free hydrocarbon compound according to invention. Catalyst poisoning is reduced and catalyst service lifetime is significantly prolonged.

Even though the branched, saturated hydrocarbon product is produced from the natural fatty acid based raw materials it contains no oxygen, thus the nitrogen oxide ($NO_x$) emissions are much lower than those of conventional biodiesel fuels.

The composition of the branched, saturated hydrocarbon product produced according the invention resembles highly those of conventional diesel fuels, thus it can be used in compression-ignition (diesel) engines with no modifications, which is not the case with fatty acid methyl ester based bio-diesel compounds.

Further, due to the pure paraffinic composition without any oxygen containing compounds, no gum is formatted in the fuel delivery systems. Engine parts are not contaminated by carbon deposits as with fatty acid methyl ester based biodiesel compounds.

The branched, saturated hydrocarbon product can be blended at any level with petroleum diesel and with fatty acid methyl ester based bio-diesel compounds. The latter may be advantageous if the lubricity of the product needs to be enhanced.

Particularly, when the process is carried out using the decarboxylation/decarbonylation route, consumption of hydrogen is reduced significantly. Decarboxylation/decarbonylation reactions decrease hydrogen consumption by 20-40%.

The invention is illustrated in the following examples presenting some preferable embodiments of the invention. However, it is evident to a person skilled in the art that the scope of the invention is not meant to be limited to these examples only.

EXAMPLES

Example 1

Skeletal Isomerisation and Deoxygenation of Tall Oil Fatty Acid

Distilled tall oil fatty acids were isomerised in a Parr high-pressure reactor with mordenite type zeolite. Tall oil fatty acids, 5 wt-% of the catalyst and 3 wt-% of water, calculated of total reaction mixture, were placed in a reactor and air was removed from the autoclave with purging nitrogen. The mixture was stirred with 300 rpm. The reactor was heated to 280° C. and kept under nitrogen atmosphere of 1.8 MPa for 6 hours. After cooling, the reaction mixture obtained was taken from the autoclave, and the zeolite was filtered off. The filtrate was distilled under reduced pressure to yield monomeric acids.

The monomeric acids thus obtained were placed in an autoclave, and double bonds were hydrogenated at 150° C. with a catalyst containing 5 wt-% Pd on carbon for 3 hours under hydrogen atmosphere of 2 MPa until the reaction was complete. Catalyst amount was 2 wt-% of monomeric acid. Then, the reaction mixture was cooled, and the catalyst was filtered off.

The obtained crude branched chain fatty acids were subjected to a conventional solvent fractionation procedure to yield isomerised fatty acids. To the crude branched chain fatty acids, about 2-fold amount by weight of hexane was added. After this mixture was cooled to −15° C., the resulting crystals were filtered off. Then, the hexane was distilled off from the filtrate to yield purified isomerised fatty acids.

In the subsequent deoxygenation step carried out by hydrodeoxygenation the isomerised fatty acids were hydrodeoxygenated in a Parr high-pressure reactor with dried and presulphided NiMo/$Al_2O_3$ catalyst to the corresponding paraffins at a hydrogen pressure of 3.3 MPa and 340° C. temperature. The amount of catalyst was 2.5 wt-% of fatty acids.

The product was a branched, mainly paraffinic hydrocarbon mixture with the properties shown in Table II. The color of the product was lightly yellow and it contained <10 ppm of sulphur originating from the HDO catalyst used in the batch hydrodeoxygenation.

Example 2

Skeletal Isomerisation and Deoxygenation of Tall Oil Fatty Acids at Lower Temperature The distilled tall oil fatty acids were isomerised, the double bonds hydrogenated and the branched, saturated fatty acids hydrodeoxygenated otherwise as in example 1 except that the reactor temperature in the hydrodeoxygenation was lower, 325° C.

A crystal clear product with properties presented in Table 3 was obtained.

Example 3

Skeletal Isomerisation of Tall Oil Fatty Acids Without Water, Deoxygenation at Lower Temperature and Cold Filtration of the End Product In the skeletal isomerisation step tall oil fatty acids and 5 wt-% of the mordenite type zeolite catalyst were mixed and air was removed from the Parr high-pressure autoclave with purging nitrogen. The mixture was stirred with 300 rpm. The reactor was heated to 275° C. and kept in a nitrogen atmosphere 0.1 MPa for 6 hours. After cooling, the reaction mixture obtained was taken out from the autoclave, and the zeolite was filtered off. The filtrate was distilled under reduced pressure to yield monomeric acids.

The double bonds of the monomeric acids thus obtained were hydrogenated as in example 1.

In the deoxygenation step the isomerised fatty acids were hydrodeoxygenated in a Parr high-pressure reactor with dried and presulphided NiMo/$Al_2O_3$ catalyst to paraffins at a hydrogen pressure of 3.3 MPa and 325° C. temperature. The amount of catalyst was 2.5 wt-% of fatty acids. The mixture was cooled to −15° C. and the resulting crystals were filtered off.

The product was a branched, mainly paraffinic hydrocarbon mixture with the properties shown in Table 3. The color of the product was crystal clear.

Example 4

Skeletal Isomerisation of Tall Oil Fatty Acids Without Water and Deoxygenation by Decarboxylation/Decarbonylation Tall oil fatty acids were isomerised and prehydrogenated as in example 3. In the deoxygenation step carried out by decarboxylation/decarbonylation the isomerised fatty acids were loaded in a Parr high-pressure reactor and the carboxyl groups were removed with dried and presulphided NiMo/$Al_2O_3$ catalyst.

Isomerised fatty acids were decarboxylated/decarbonylated to paraffins at a gas pressure of 0.3 MPa and 335° C. temperature. The amount of catalyst was 2.5 wt-% of fatty acids. The gas consisted of 10% hydrogen in nitrogen.

The product was a branched, mainly paraffinic hydrocarbon mixture with the carbon chain length typically one carbon atom less than in the hydrodeoxygenation and with the properties shown in Table 3. The color of the product was crystal clear.

TABLE 3

Properties of hydrocarbon products

| Method | Analysis | Example 1 | Example 2 | Example 3 | Example 4 |
|---|---|---|---|---|---|
| ASTM D4052 | Density 15° C., kg/m$^3$ | 811 | 809 | 799 | 800 |
| ASTM D2887 | Distillation Start ° C. | 245 | 219 | 225 | 117 |
| | 5%, ° C. | 277 | 281 | 270 | 170 |
| | 10%, ° C. | 283 | 286 | 280 | 195 |
| | 30%, ° C. | 294 | 293 | 294 | 262 |
| | 50%, ° C. | 300 | 296 | 300 | 271 |
| | 70%, ° C. | 309 | 310 | 309 | 283 |
| | 90%, ° C. | 326 | 337 | 323 | 301 |
| | 95%, ° C. | 362 | 443 | 357 | 312 |
| | End, ° C. | 486 | 507 | 481 | 355 |
| ASTM D445 | kV 40, cSt | 4.0 | 4.4 | 3.8 | 2.4 |
| | n-Paraffins GC wt-% | 6 | 15 | 7 | 11 |
| | Paraffinic C IR wt-% | >70 | | >70 | 70 |
| | Naphtenic C IR wt-% | | | | 24 |
| | Aromatic C IR wt-% | 14 | | 7 | 6 |
| ASTM D3120 | S, mg/kg | 9 | | <1 | |
| ASTM D4629 | N, mg/kg | <1 | | <1 | |

TABLE 3-continued

Properties of hydrocarbon products

| Method | Analysis | Example 1 | Example 2 | Example 3 | Example 4 |
|---|---|---|---|---|---|
| EN 22719 | Flash point PMcc, °C. | 141 | 138 | 139 | 67 |
| | IQT cetane number | 93 | 78 | 93 | 60 |
| EN 116 | Cold Filter Plug Point ° C. | −39 | −31 | −35 | −45 |
| ASTM D5773 D5771 | Cloud Point, ° C. | −32 | −29 | −29 | −42 |
| IP 391 | Aromatics % (mainly mono) | 16.1 | | 7.8 | 5.8 |

The invention claimed is:

1. A process for the manufacture of branched saturated hydrocarbons, wherein the process comprises the steps where a feedstock comprising unsaturated fatty acids or fatty acid $C_1$-$C_5$ alkyl esters or mixtures thereof is subjected to skeletal isomerization to yield branched fatty acids or fatty acid $C_1$-$C_5$ alkyl esters or mixtures thereof, which are then deoxygenated to branched hydrocarbons.

2. The process according to claim 1, wherein the feedstock comprises at least 20% by weight of unsaturated fatty acids or fatty acid $C_1$-$C_5$ alkyl esters.

3. The process according to claim 1, wherein the unsaturated fatty acids or fatty acid $C_1$-$C_5$ alkyl esters used as the feedstock have a total carbon number of 8 to 26.

4. The process according to claim 1, wherein the feedstock originates from biological raw materials.

5. The process according to claim 1, wherein the skeletal isomerization step is carried out at a temperature of 150-400° C., under the pressure of 0-5 MPa.

6. The process according to claim 1, wherein the skeletal isomerization step is carried out in the presence of an acidic catalyst selected from the group consisting of silico alumino phosphates and zeolites.

7. The process according to claim 1, wherein 0-8% by weight of water or $C_1$-$C_5$ alcohol, based on the total reaction mixture, is added to the feedstock.

8. The process according to claim 1, wherein after the skeletal isomerization step a prehydrogenation step is carried out.

9. The process according to claim 8, wherein the prehydrogenation step is carried out in the presence of a hydrogenation catalyst comprising one or more Group VIII and/or VIA metals, at a temperature of 50-400° C. under a hydrogen pressure of 0.1-20 MPa.

10. The process according to claim 8, wherein when the feedstock comprises fatty acid $C_1$-$C_5$ alkyl esters, the prehydrogenation step is carried out in the presence of a metal catalyst at 25-30 MPa hydrogen pressure and at temperature of 200-230° C.

11. The process according to claim 1, wherein the product obtained from the skeletal isomerization and optional prehydrogenation steps is subjected to the deoxygenation step, which is carried out by decarboxylation/decarbonylation or hydrodeoxygenation.

12. The process according to claim 11, wherein in the decarboxylation and/or decarbonylation step(s), the product and optionally a solvent or a mixture of solvents are brought into contact with a heterogeneous decarboxylation/decarbonylation catalyst selected from supported catalysts comprising one or more Group VIII and/or VIA metals of the Periodic Table, at a temperature of 100-400° C. under a pressure from atmospheric pressure to 20 MPa of inert gas/hydrogen-mixture.

13. The process according to claim 12, wherein the heterogeneous decarboxylation and/or decarbonylation catalyst is Pd on carbon or sulphided NiMo on alumina.

14. The process according to claim 11, wherein in the hydrodeoxygenation step, the product and optionally a solvent or a mixture of solvents are brought into contact with a hydrogenation catalyst comprising a metal from Group VIII and/or VIA of the Periodic Table under a pressure between 1 and 20 MPa, and at a temperature between 200 and 500° C.

15. The process according to claim 14, wherein the hydrodeoxygenation catalyst is a supported Pd, Pt, Ni, NiMo or a CoMo catalyst and the support is alumina and/or silica.

16. The process according to claim 11, wherein in the decarboxylation/decarbonylation and/or hydrodeoxygenation step(s), the solvent is selected from the group consisting of hydrocarbons and recycled process streams comprising hydrocarbons.

17. The process according to claim 2, wherein the unsaturated fatty acids or fatty acid $C_1$-$C_5$ alkyl esters used as the feedstock have a total carbon number of 8 to 26.

18. The process according to claim 2, wherein the feedstock originates from biological raw materials.

19. The process according to claim 3, wherein the feedstock originates from biological raw materials.

20. The process according to claim 1, wherein the feedstock comprises at least 50% by weight of unsaturated fatty acids or fatty acid $C_1$-$C_5$ alkyl esters.

21. The process according to claim 1, wherein the unsaturated fatty acids or fatty acid $C_1$-$C_5$ alkyl esters used as the feedstock have a total carbon number of 12 to 20.

22. The process according to claim 1, wherein the skeletal isomerization step is carried out at a temperature of 200-350° C., under the pressure of 0.1-5 MPa.

23. The process according to claim 1, wherein the skeletal isomerization step is carried out in the presence of an acidic catalyst selected from the group consisting of faujasite, offeretite, montmorillonite and mordenite.

24. The process according to claim 1, wherein 1-3% by weight of water or $C_1$-$C_5$ alcohol, based on the total reaction mixture, is added to the feedstock.

25. The process according to claim 8, wherein the prehydrogenation step is carried out in the presence of a hydrogenation catalyst comprising one or more Group VIII and/or VIA metals, at a temperature of 150-250° C. under a hydrogen pressure of 1-10 MPa.

26. The process according to claim 8, wherein when the feedstock comprises fatty acid $C_1$-$C_5$ alkyl esters, the prehydrogenation step is carried out in the presence of a copper-chromite catalyst or chrome, ferrous or rhodium activated nickel catalyst at 25-30 MPa hydrogen pressure and at temperature of 200-230° C.

27. The process according to claim 11, wherein in the decarboxylation and/or decarbonylation step(s), the product and optionally a solvent or a mixture of solvents are brought into contact with a heterogeneous decarboxylation/decarbonylation catalyst selected from supported catalysts comprising one or more Group VIII and/or VIA metals of the Periodic Table, at a temperature of 250-350° C. under a pressure from 0.1 to 5 MPa of inert gas/hydrogen-mixture.

28. The process according to claim 11, wherein in the hydrodeoxygenation step, the product and optionally a solvent or a mixture of solvents are brought into contact with a hydrogenation catalyst comprising a metal from Group VIII and/or VIA of the Periodic Table under a pressure between 2 and 10 MPa, and at a temperature between 250 and 350° C.

29. The process according to claim 14, wherein the hydrodeoxygenation catalyst is $NiMo/Al_2O_3$ or $CoMo/Al_2O_3$.

30. The process according to claim 11, wherein in the decarboxylation/decarbonylation and/or hydrodeoxygenation step(s), the solvent is selected from the group consisting of paraffin, isoparaffin, naphthene, an aromatic hydrocarbon having a boiling range of 150-350° C., and mixtures thereof.

31. The process according to claim 2, wherein the unsaturated fatty acids or fatty acid $C_1$-$C_5$ alkyl esters used as the feedstock have a total carbon number of 12 to 20.

* * * * *